(12) United States Patent
Murphy

(10) Patent No.: US 11,284,960 B2
(45) Date of Patent: Mar. 29, 2022

(54) PACKAGING CONTAINER FOR A MEDICAL DEVICE

(71) Applicant: M_MICROTECHNOLOGIES, INC., Pompano Beach, FL (US)

(72) Inventor: Jason Murphy, Grand Rapids, MI (US)

(73) Assignee: M_MICROTECHNOLOGIES, INC., Pompano Beach, FL (US)

( * ) Notice: Subject to any disclaimer, the term of this patent is extended or adjusted under 35 U.S.C. 154(b) by 51 days.

(21) Appl. No.: 16/879,017

(22) Filed: May 20, 2020

(65) Prior Publication Data
US 2021/0361373 A1  Nov. 25, 2021

(51) Int. Cl.
A61B 50/30 (2016.01)
B65D 43/16 (2006.01)
B65D 51/22 (2006.01)

(52) U.S. Cl.
CPC ............ A61B 50/30 (2016.02); B65D 43/162 (2013.01); B65D 51/22 (2013.01); B65D 2543/00064 (2013.01); B65D 2543/00296 (2013.01)

(58) Field of Classification Search
CPC ... A61B 50/30; A61B 43/162; A61B 50/3001; A61B 2050/3002; B65D 43/162; B65D 51/22; B65D 2543/00064; B65D 2543/00296
USPC ....... 206/438, 207, 212, 571, 352, 364, 365, 206/477
See application file for complete search history.

(56) References Cited

U.S. PATENT DOCUMENTS

| 3,035,691 A | 5/1962 | Kai et al. |
| 3,207,302 A * | 9/1965 | Hobbs ................... A61M 5/002 206/366 |
| 3,613,879 A | 10/1971 | Kemble |
| 3,761,013 A | 9/1973 | Schuster |

(Continued)

FOREIGN PATENT DOCUMENTS

| EP | 2571782 B1 | 9/2015 |
| WO | WO 2012/166381 A1 | 12/2012 |
| WO | WO 2016/177856 A1 | 11/2016 |

OTHER PUBLICATIONS

"Specific Holders"; https://www.selenium-medical.com/selenium-packaging/specific-holders/; accessed Mar. 7, 2020; 1 page.

(Continued)

Primary Examiner — Rafael A Ortiz
(74) Attorney, Agent, or Firm — BakerHostetler

(57) ABSTRACT

A packaging container for a protected instrument (such as a medical device) includes: (a) first and second complementary clam-shell container components; (b) a cradle for seating a protected instrument formed into the interior side the first clam-shell container component, where the cradle is surrounded on at least three sides by weakened lines formed into first clam-shell container component; (c) a pull-tab extending from the exterior side of the first clam-shell container component, where the pull-tab is positioned within the weakened lines; and (d) a protected instrument seated on the cradle. The first and second complementary clam-shell container components are closed together to enclose the cradle and the protected instrument therein, and the first and second complementary clam-shell components are then fixed together about their respective outer peripheral edge surfaces.

25 Claims, 4 Drawing Sheets

(56) References Cited

U.S. PATENT DOCUMENTS

| | | | |
|---|---|---|---|
| 3,889,808 A | 6/1975 | Helms | |
| 3,926,309 A | 12/1975 | Center | |
| 3,972,418 A | 8/1976 | Schuler et al. | |
| 4,005,776 A * | 2/1977 | Seeley | B65D 75/366 206/306 |
| 4,106,621 A | 8/1978 | Sorenson | |
| 4,216,860 A | 8/1980 | Heimann | |
| 4,960,240 A | 10/1990 | McElfresh | |
| 5,133,454 A * | 7/1992 | Hammer | A61M 5/002 206/364 |
| 5,407,070 A * | 4/1995 | Bascos | A61M 5/002 206/364 |
| 5,566,828 A * | 10/1996 | Claes | A61M 5/003 206/570 |
| 6,595,362 B2 * | 7/2003 | Penney | A61M 5/002 206/364 |
| 6,892,881 B2 | 5/2005 | Leitch | |
| 7,328,794 B2 | 2/2008 | Lubs et al. | |
| 7,434,686 B2 * | 10/2008 | Prindle | A61M 5/002 206/364 |
| 7,597,196 B2 * | 10/2009 | Langone | A61M 5/002 206/364 |
| 7,931,167 B2 * | 4/2011 | Chmela | B65D 41/48 220/270 |
| 8,523,843 B2 * | 9/2013 | Kavanagh | A61M 25/0111 604/544 |
| 8,584,849 B2 * | 11/2013 | McCaffrey | A61M 25/002 206/364 |
| 8,734,420 B2 * | 5/2014 | Ariagno | A61J 1/2089 604/414 |
| 8,794,470 B2 * | 8/2014 | Wambeke | B65D 43/0256 220/270 |
| 9,333,289 B1 * | 5/2016 | Hirschmann | B65D 55/06 |
| 9,676,537 B2 | 6/2017 | Fenech, III et al. | |
| 2005/0167311 A1 | 8/2005 | Tonsfeldt et al. | |
| 2006/0032773 A1 * | 2/2006 | Booker | B65D 25/105 206/446 |
| 2007/0102317 A1 | 5/2007 | Crawford et al. | |
| 2010/0002963 A1 | 1/2010 | Holbert et al. | |
| 2010/0278454 A1 | 11/2010 | Huffer | |
| 2011/0218433 A1 | 9/2011 | Speeg et al. | |
| 2011/0253718 A1 | 10/2011 | Sierra-Gomez et al. | |
| 2013/0062342 A1 | 3/2013 | Hansen et al. | |
| 2015/0136632 A1 * | 5/2015 | Moir | B65D 43/165 206/470 |
| 2018/0311027 A1 * | 11/2018 | Distefano | A61B 17/865 |

OTHER PUBLICATIONS

"Hinged clamshell container"; www.china-clamshell.com/hinged-clamshell-container-P442.htm; accessed Mar. 9, 2020; 2 pages.

https://medical.placon.com/wp-content/uploads/2014/b_big_product_lids.jpg; access Mar. 9, 2020; 1 page.

"Gun holsters clamshell packaging—Creativeclamshell Packaging"; https://www.creativeclamshell.com/product/gun-holsters-clamshell-packaging.html; Kesheng Custom Packaging Solutions; accessed Mar. 9, 2020; 3 pages.

"Packaging of New Generation Biological Products with Films and Foils"; Sabre Medical; Mar. 2019; 2 pages.

"Intuitive PETG Thermoformed Package Shines for NorthStar"; Healthcare Packing; Jul. 2016; 1 page.

"Daryl Humphrey's Pill Box Design is Better Suited to the Elderly Laura McQuarrie"; https://www.trendhunter.com/trends/pill-box-design; Nov. 2014; 1 pages.

Creative Blog Staff; "Clever new pill packaging is much easier to open"; https://www.creativeblog.com/packaging/clever-new-pill-packaging-much-easier-open-101413231; Oct. 2014; accessed Jul. 10, 2020; 27 pages.

* cited by examiner

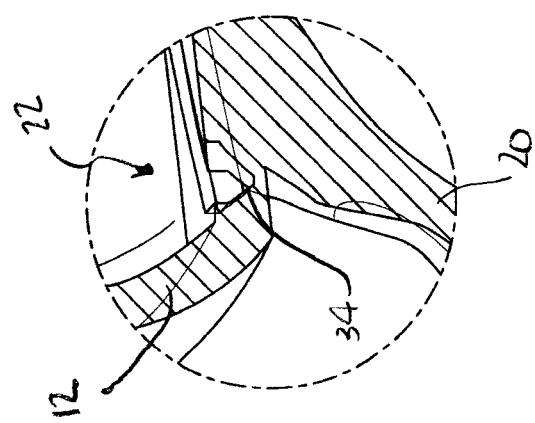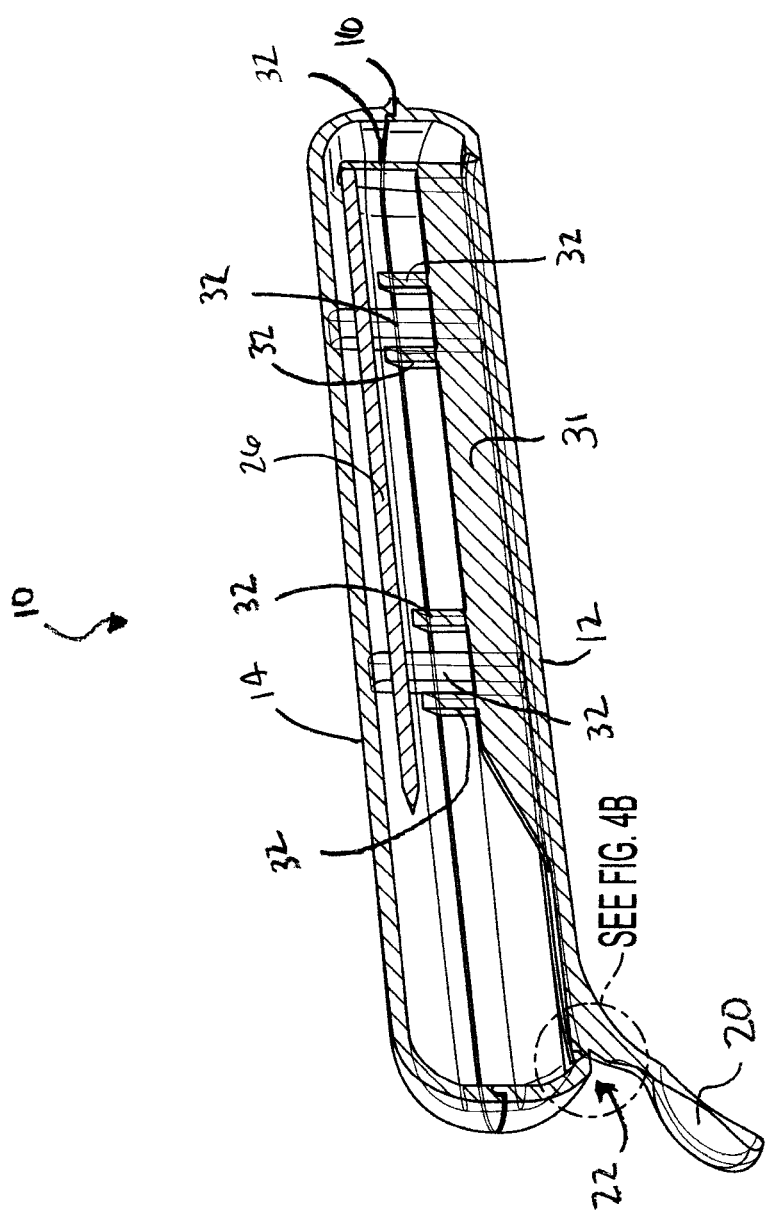
FIG. 4B
FIG. 4A

PACKAGING CONTAINER FOR A MEDICAL DEVICE

BACKGROUND

The current disclosure is directed to a packaging and presentation container for a protected instrument, such as a medical device; and associated method for creating the packaging and presentation container.

SUMMARY

In a first aspect, a packaging container for a protected instrument is provided. The packaging container includes (a) first and second complementary clam-shell container components, where each first and second complementary clam-shell container component have a concave side, a convex side and an outer peripheral edge surface; (b) a cradle for seating a protected instrument formed into the concave side the first clam-shell container component, where the cradle is surrounded on at least three sides by weakened lines formed into first clam-shell container component and on a fourth side by a first living hinge formed into the first clam-shell container component; (c) a pull-tab extending from the convex side of the first clam-shell container component, the pull-tab positioned opposite the first living hinge and positioned within the weakened lines; and (d) a protected instrument seated on the cradle; where the first and second complementary clam-shell container components are closed together to enclose the cradle and the protected instrument therein, and the first and second complementary clam-shell components are sealed together about their respective outer peripheral edge surfaces. To open and present the protected instrument to the user, upon pulling the pull-tab by the user, the weakened lines will tear allowing the cradle to flip open on the first living hinge presenting the protected instrument to the user. In a more detailed embodiment, the packaging container further includes (e) a second living hinge connecting the first and second complementary clam-shell container components together at an end thereof. In a further detailed embodiment, the first and second complementary clam-shell container components and the second living hinge are an integrally molded thermoplastic piece. In yet a further detailed embodiment, the thermoplastic is a generally clear thermoplastic. In yet a further detailed embodiment, the cradle is also integrally molded into the thermoplastic piece.

In another detailed embodiment to the first aspect, the first and second complimentary clam-shell components are sealed together about their periphery by an ultrasonic weld. Alternatively, or in addition, the cradle comprises a plurality of posts extending within the concave side of the first clam-shell container component. Alternatively, or in addition, the weakened lines formed in the first clam-shell container component comprise a decreased thickness of a wall of the first clam-shell container component. Alternatively, or in addition, the decreased thickness of the wall of the first clam-shell container component comprising the weakened lines is provided by a groove formed in the concave side of the first clam-shell container component along the weakened lines.

In another detailed aspect, the first and second complementary clam-shell container components are elongated so that the first and second complementary clam-shell container components close together to form an elongated capsule, and the first living hinge is positioned approximate a first longitudinal end of the capsule and the pull-tab is positioned approximate the opposite longitudinal end of the capsule.

It is a second aspect to provide a method for packaging a protected instrument, the method includes the following steps: (1) providing (a) first and second complementary clam-shell container components, each first and second complementary clam-shell container component having a concave side, a convex side and an outer peripheral edge surface, (b) a cradle for seating a protected instrument formed into the concave side the first clam-shell container component, the cradle being surrounded on at least three sides by weakened lines formed into first clam-shell container component, and (c) a pull-tab extending from the convex side of the first clam-shell container component, the pull-tab positioned within the weakened lines; (2) seating a protected instrument on the cradle; (3) closing the first and second complementary clam-shell container components together to enclose the cradle and the protected instrument therein; and (4) sealing the first and second complementary clam-shell components together about their respective outer peripheral edge surfaces. In a detailed embodiment, the method further includes the step of integrally molding the first and second complementary clam-shell container components and the second living hinge from a thermoplastic material. In a further detailed embodiment, the molding step further integrally molds the cradle into the thermoplastic piece. Alternatively, or in addition, the molding step further integrally molds the pull-tab and the weakened lines in the first clam-shell container component. Alternatively, or in addition, the molding step molds a decreased thickness of a wall of the first clam-shell container component to form the weakened lines in the first clam-shell container component. Alternatively, or in addition, the sealing step comprises an ultrasonic welding step.

In a third aspect, a packaging container for a protected instrument includes: (a) first and second complementary clam-shell container components, at least the first complementary clam-shell container component having an interior side, an exterior side and an outer peripheral edge surface; (b) a cradle for seating a protected instrument formed into the interior side the first clam-shell container component, where the cradle is surrounded on at least three sides by weakened lines formed into first clam-shell container component; (c) a pull-tab extending from the exterior side of the first clam-shell container component, where the pull-tab is positioned within the weakened lines; and (d) a protected instrument seated on the cradle; where the first and second complementary clam-shell container components are closed together to enclose the cradle and the protected instrument therein, and the first and second complementary clam-shell components are fixed together about their respective outer peripheral edge surfaces. In such an aspect, upon pulling the pull-tab by a user, the weakened lines will tear allowing the cradle to pull away from the first clam-shell container component, presenting the protected instrument to the user.

BRIEF DESCRIPTION OF THE DRAWINGS

FIG. 4A is a cross-sectional view of the embodiments of FIGS. 1-3 shown in the closed orientation enclosing the medical device therein; and FIG. 4B is a magnified view of the area of FIG. 4A enclosed by a phantom-circle.

DETAILED DESCRIPTION

Figure 1:
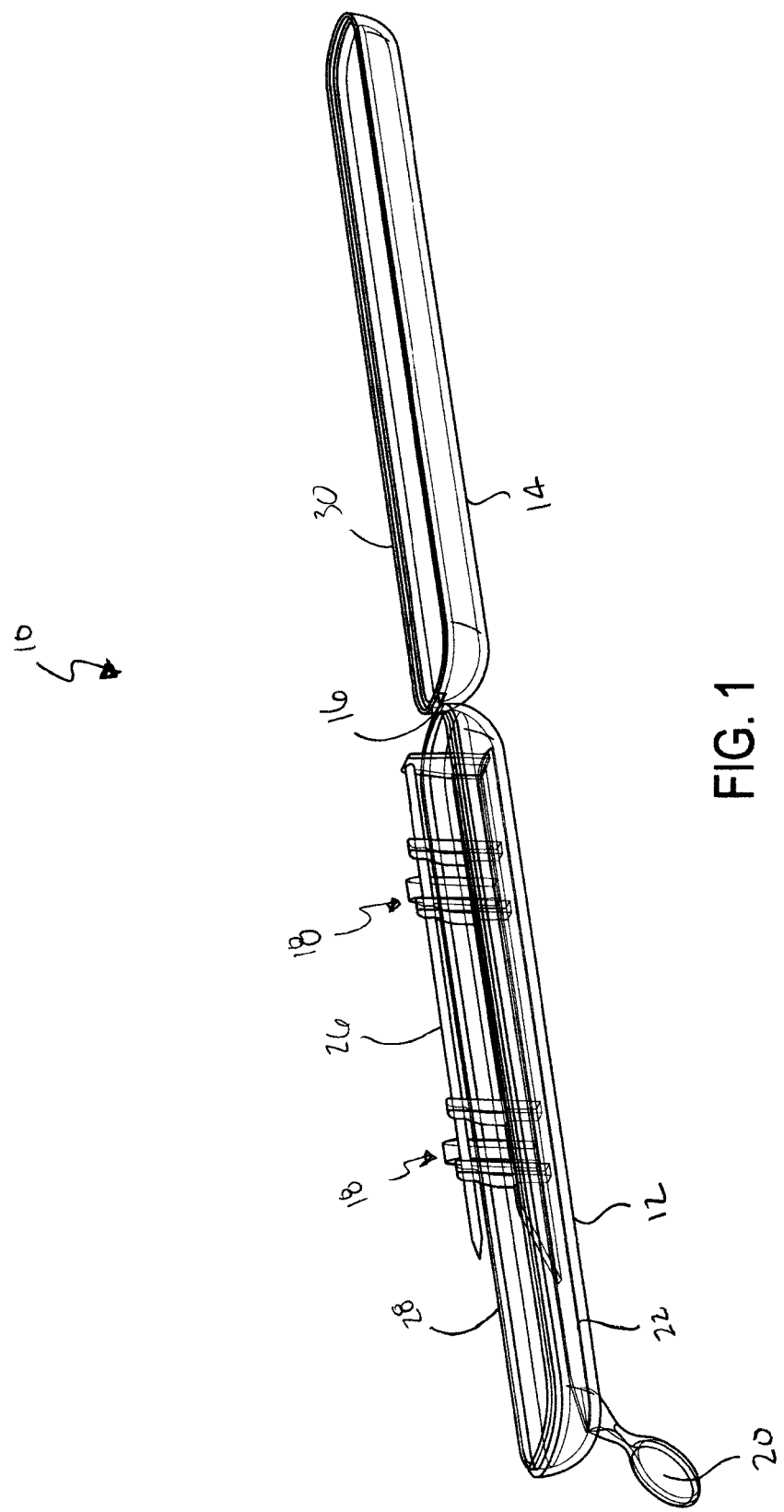
FIG. 1 is a perspective view of an exemplary embodiment of the packaging container according to the current disclosure shown in an open orientation following thermoplastic molding with a medical device seated on the cradle.

As shown in the figures, an exemplary embodiment of the packaging container 10 includes first and second complimentary clam-shell container components 12, 14 connected together by a living hinge 16. On the interior concave surface of the first clam-shell container component 12 is provided a cradle 18 for seating a medical instrument. The first and second complimentary claim-shell container components 12, 14, the living hinge 16 and the cradle 18 are molded as a unitary component from a clear thermoplastic material.

Figure 2:
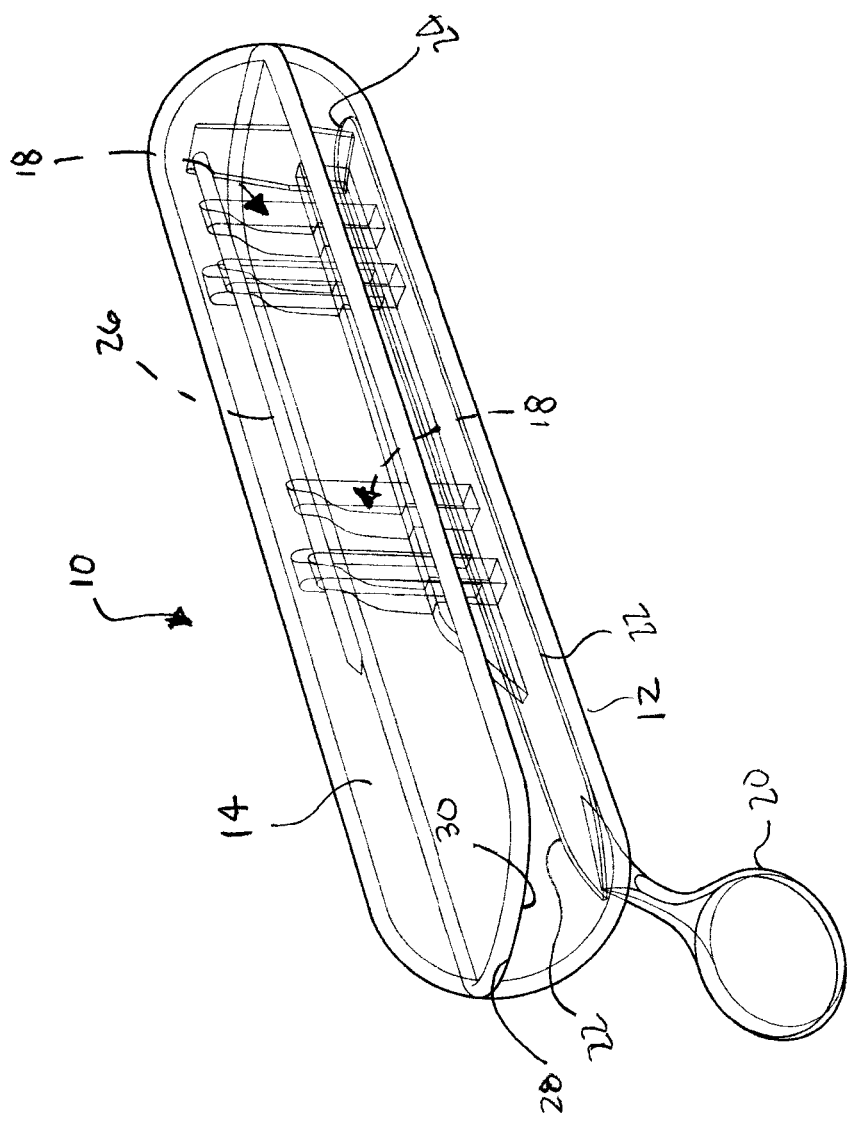
FIG. 2 is a perspective view of the embodiment of FIG. 1 shown in the closed orientation enclosing the medical device therein.
Figure 3:
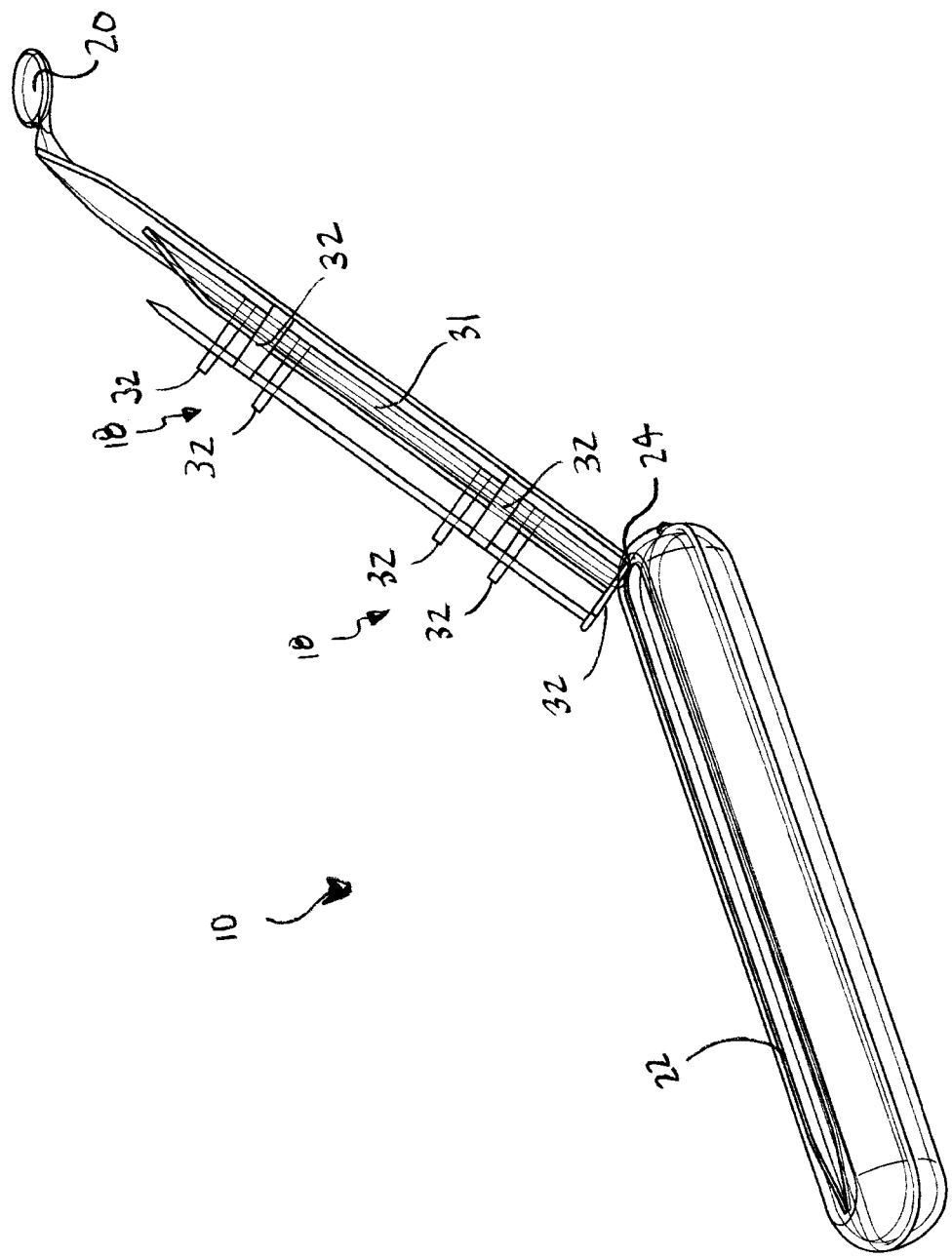
FIG. 3 is a perspective view of the embodiment of FIGS. 1 and 2 showing the tear-away portion of the packaging opening up to present the medical device to the user.

As shown specifically in FIGS. 2 and 3, the cradle 18 is surrounded on at least three sides by weakened lines 22 formed into the first clam-shell container component 12 and surrounded on a fourth side by a living hinge 24 formed into the first clam-shell container component 12 (as another way of describing, the weakened lines 22 surround at least 270° of the cradle 18 while the living hinge 24 surrounds the remainder). A pull tab 20 extends from the convex side of the first clam-shell container component 12 and is positioned opposite the first living hinge 24 and is also positioned within the weakened lines 22.

To assemble the packaging container 10 with the medical device, the unitary component comprising the first and second complimentary clam-shell container components 12, 14, the living hinge 16 and the cradle 18 is molded in an open configuration as shown in FIG. 1. Next, the medical device 26 is placed on the cradle. Next, the first and second complimentary clam-shell container components 12, 14 are closed together about hinge 16 to enclose the cradle and the medical device 26 therein. Then the first and second complimentary clam-shell container components 12,14 are sealed together about their respective outer peripheral edge surfaces 28, 30 by ultrasonic welding. FIG. 2 shows the packaging container after the first and second complimentary clam-shell container components have been closed together and sealed about their outer peripheral edge surfaces. At this stage, the packaging container 10 with the contained/protected medical device 26 is ready for distribution to end-users.

To open the packaging 10 by a user, as shown in FIG. 3, the user will pull on the pull tab 20 to tear the weakened tear lines 22 formed into the first clam-shell container component 12 allowing the cradle 18 to flip open on the living hinge 24 presenting the medical device 26 to the user.

As shown in FIG. 3, the exemplary cradle 18 includes a longitudinal support beam 31 running longitudinally along the area within the weakened tear lines 22 and also includes a plurality of posts 32 extending up from the support beam 31, where the medical device is supported on the plurality of the posts 32 in use. Those of ordinary skill will understand that a multitude of alternate cradle designs are available to seat a corresponding multitude of various protected instruments thereon. The exemplary cradle 18 is specifically designed to seat a pipette medical device. Alternate cradle designs will be apparent to those of ordinary skill. The claims are not to be limited to any specific cradle design unless expressly recited within the claim.

As shown in greater detail in FIGS. 4A and 4B, the weakened lines 22 are formed by molding a groove 34 into the concave surface of the first clam-shell container component 12 along the tear lines 22. This groove provides a thinner wall at the bottom of the groove where this thinned wall is substantially weakened in comparison to the remainder of the first clam-shell container component, thereby tearing when a user provides sufficient pulling force on the pull tab 20.

In the current embodiment, the first and second complimentary clam-shell container components 12, 14 are elongated so that the first and second complimentary clam-shell container components close together to form an elongated capsule. Further, in this embodiment, the first living hinge 24 is positioned approximate a first longitudinal end of the capsule and the pull tab 20 is positioned approximate the opposite longitudinal end of the capsule. Those of ordinary skill will understand that a multitude of alternate container shapes are available to contain a corresponding multitude of various protected instruments thereon. The exemplary capsule-shaped packaging 10 is specifically designed to contain a pipette medical device. Alternate packaging designs will be apparent to those of ordinary skill. The claims are not to be limited to any specific packaging design unless expressly recited within the claim. It is also to be understood that alternate embodiments may be designed to contain more than one protected instrument. For example, an alternate packaging design my include a plurality of cradles and a corresponding plurality of tear-away presentation mechanisms as discussed above. It should also be understood that it is not necessary for each of the clam-shell container components 12,14 to have concavities—for example, it is within the scope of the disclosure that one of the clam-shell container components is designed to be planar.

In the current embodiment, the medical device 26 is a pipette. Nevertheless, the current disclosure is not limited to any specific type of medical device; and in certain embodiments, the current disclosure is not limited to medical devices. For example, any type of device to be stored in a protected manner and to be made available to a user upon opening the packaging as disclosed herein is within the scope of the current disclosure. Such protected instruments may include (without limitation) medical devices, lab instruments, electronic devices, electronic instruments, pharmaceuticals, food products, diagnostic instruments, and the like.

In an exemplary embodiment, the packaging container is a one-time use, where the materials are selected to be recyclable.

What is claimed is:

1. A packaging container for a protected instrument, comprising:

first and second complementary clam-shell container components, each first and second complementary clam-shell container component having a concave side, a convex side and an outer peripheral edge surface;

a cradle for seating a protected instrument formed into the concave side the first clam-shell container component, the cradle being surrounded on at least three sides by weakened lines formed into first clam-shell container component and on a fourth side by a first living hinge formed into the first clam-shell container component;

a pull-tab extending from the convex side of the first clam-shell container component, the pull-tab positioned opposite the first living hinge and positioned within the weakened lines; and a protected instrument seated on the cradle;

the first and second complementary clam-shell container components being closed together to enclose the cradle and the protected instrument therein, and the first and second complementary clam-shell components being sealed together about their respective outer peripheral edge surfaces;

whereby, upon pulling the pull-tab by a user, the weakened lines will tear allowing the cradle to flip open on the first living hinge presenting the protected instrument to the user.

2. The packaging container of claim 1, further comprising a second living hinge connecting the first and second complementary clam-shell container components together at an end thereof.

3. The packaging container of claim 2, wherein the first and second complementary clam-shell container components and the second living hinge are an integrally molded thermoplastic piece.

4. The packaging container of claim 3, wherein the thermoplastic is a generally clear thermoplastic.

5. The packaging container of claim 3, wherein the cradle is also integrally molded into the thermoplastic piece.

6. The packaging container of claim 1, wherein the first and second complimentary clam-shell components are sealed together about their periphery by an ultrasonic weld.

7. The packaging container of claim 1, wherein the cradle comprises a plurality of posts extending within the concave side of the first clam-shell container component.

8. The packaging container of claim 1, wherein the weakened lines formed in the first clam-shell container component comprise a decreased thickness of a wall of the first clam-shell container component.

9. The packaging container of claim 8, wherein the decreased thickness of the wall of the first clam-shell container component comprising the weakened lines is provided by a groove formed in the concave side of the first clam-shell container component along the weakened lines.

10. The packaging container of claim 1, wherein the first and second complementary clam-shell container components are elongated so that the first and second complementary clam-shell container components close together to form an elongated capsule, and the first living hinge is positioned approximate a first longitudinal end of the capsule and the pull-tab is positioned approximate the opposite longitudinal end of the capsule.

11. The packaging container of claim 1, wherein the protected instrument is a medical device.

12. The packaging container of claim 1, wherein the first and second complimentary clam-shell container components are formed from a generally clear thermoplastic material.

13. A method for packaging a protected instrument, comprising the steps of:

providing (a) first and second complementary clam-shell container components, each first and second complementary clam-shell container component having a concave side, a convex side and an outer peripheral edge surface, (b) a cradle for seating a protected instrument formed into the concave side the first clam-shell container component, the cradle being surrounded on at least three sides by weakened lines formed into first clam-shell container component, and (c) a pull-tab extending from the convex side of the first clam-shell container component, the pull-tab positioned within the weakened lines;

seating a protected instrument on the cradle;

closing the first and second complementary clam-shell container components together to enclose the cradle and the protected instrument therein; and sealing the first and second complementary clam-shell components together about their respective outer peripheral edge surfaces.

14. The method of claim 13, wherein the cradle is surrounded on a fourth side by a living hinge formed into the first clam-shell container component, and wherein the pull-tab is positioned opposite the living hinge within the weakened lines.

15. The method of claim 13, further comprising a living hinge connecting the first and second complementary clam-shell container components together at an end thereof.

16. The method of claim 15, further comprising the step of integrally molding the first and second complementary clam-shell container components and the second living hinge from a thermoplastic material.

17. The method of claim 16, wherein the thermoplastic material is a generally clear thermoplastic.

18. The method of claim 16, wherein the molding step further integrally molds the cradle into the thermoplastic piece.

19. The method of claim 13, wherein the molding step further integrally molds the pull-tab and the weakened lines in the first clam-shell container component.

20. The method of claim 19, wherein the molding step molds a decreased thickness of a wall of the first clam-shell container component to form the weakened lines in the first clam-shell container component.

21. The method of claim 20, wherein the decreased thickness of the wall of the first clam-shell container component comprising the weakened lines is provided by a groove molded into the concave side of the first clam-shell container component along the weakened lines.

22. The method of claim 13, wherein the sealing step comprises an ultrasonic welding step.

23. The method of claim 13, wherein the cradle comprises a plurality of posts extending within the concave side of the first clam-shell container component.

24. The method of claim 13, wherein the protected instrument is a medical device.

25. A packaging container for a protected instrument, comprising:

first and second complementary clam-shell container components, at least the first complementary clam-shell container component having an interior side, an exterior side and an outer peripheral edge surface;

a cradle for seating a protected instrument formed into the interior side the first clam-shell container component, the cradle being surrounded on at least three sides by weakened lines formed into first clam-shell container component;

a pull-tab extending from the exterior side of the first clam-shell container component, the pull-tab positioned within the weakened lines; and a protected instrument seated on the cradle;

the first and second complementary clam-shell container components being closed together to enclose the cradle and the protected instrument therein, and the first and second complementary clam-shell components being fixed together about their respective outer peripheral edge surfaces;

whereby, upon pulling the pull-tab by a user, the weakened lines will tear allowing the cradle to pull away from the first clam-shell container component, presenting the protected instrument to the user.

* * * * *